US00PP09640P

United States Patent [19]

Eubanks

[11] Patent Number: Plant 9,640

[45] Date of Patent: Sep. 3, 1996

[54] CORN PLANT NAMED 'SUN STAR'

[76] Inventor: Mary W. Eubanks, 4110 Hulon Dr., Durham, N.C. 27705

[21] Appl. No.: 455,327

[22] Filed: May 31, 1995

[51] Int. Cl.[6] ..... A01H 5/00

[52] U.S. Cl. ..... Plt./100

[58] Field of Search ..... Plt./100; 800/200

[56] References Cited

U.S. PATENT DOCUMENTS

P.P. 6,906 7/1989 Eubanks ..... Plt./100

P.P. 7,977 9/1992 Eubanks ..... Plt./100

5,330,547 7/1994 Eubanks ..... 47/58

*Primary Examiner*—James R. Feyrer

[57] ABSTRACT

A new and distinct corn plant which is the product of a cross between diploid *Tripsacum dactyloides* and *Zea diploperennis,* a diploid perennial teosinte. This plant is fertile, has proven to be cross compatible with *Zea mays* L. and offers an avenue to expand the gene pool for commercial corn varieties. The instant plant is perennial, offers resistance to corn rootworm, remarkable drought tolerance, and prolific production of fruit.

6 Drawing Sheets

BACKGROUND OF THE NEW PLANT

Two wild grasses, perennial teosinte, *Zea diploperennis* Iltis, Doebley and Guzman, and Eastern gamagrass, *Tripsacum dactyloides* L. have been crossed to produce a fully fertile bridge species that may improve corn, *Zea mays* L., by conferring beneficial traits such as pest resistance and drought tolerance. *Z. diploperennis* (hereafter referred to as diploperennis), was an unkown wild relative of corn until it was discovered, apparently on the threshold of extinction, in the mountains of Jalisco, Mexico in the late 1970's. It is in the same genus as corn, has the same chromosome number as corn (n=10), and hybridizes easily with it. Gamagrass is a more distant relative of corn with a different haploid chromosome number (n=18), and varying ploidy levels ranging from 2n=36 to 2n=108. Tripsacum has been crossed with corn by artificial techniques and hybrids obtained are male sterile and essentially female sterile. All attempts to cross Tripsacum and annual teosinte, the closest relative of corn that some scientists believe is its wild progenitor, failed. Many plant breeders believe that Tripsacum has significant potential for improving corn by expanding its genetic diversity.

In 1984, crosses were made by pollinating diploperennis with pollen from a tetraploid (2n=72) *T. dactyloides*. U.S. Plant Pat. No. 6,906 for Sun Dance, the hybrid from that cross, was issued Jul. 4, 1989. In April, 1985, the reciprocal cross to the tetraploid Tripsacum was made using diploperennis pollen, and U.S. Plant Pat. No. 7,977 for Tripsacorn, the hybrid from that cross, was issued Sep. 15, 1992. U.S. Pat. No. 5,330,547, a utility patent on the method for transferring Tripsacum nuclear and cytoplasmic genes into maize via Tripsacorn, was issued Jul. 19, 1994. Ser. No. 08/248,333, filed May 24, 1994, is a continuation of the utility patent involving hybrid material, derived from a Tripsacum female parent pollinated by diploperennis, in crosses to maize.

On Jan. 18, 1988, pistillate inflourescences on a diploperennis plant were pollinated with pollen from a distinctly different *T. dactyloides* that is a diploid (2n–36) rather than a tetraploid plant. The seed was harvested and stored until Jan. 18, 1992, when it was germinated. The seed had been stored for four years because it was pale in color and did not appear viable. Earlier attempts to germinate seed obtained from crossing diploperennis and Tripsacum plants that were not tetraploid had failed. The reason I attempted to germinate the seed in 1992 was I decided to cull all old seed from earlier crosses. As a precaution, I never throw out seed until I run it through a standard germination test. Much to my surprise a single seed from this cross germinated and grew to produce a normal, fully fertile plant that is perennial and produces viable fruits twice annually.

Sun Star has been propagated by rhizome divisions and cuttings. Crosses have been made to inbred corn line W64A. Sun Star is similar to Sun Dance and Tripsacorn, hybrids derived from crossing tetraploid Tripsacum with diploperennis, in that it is fertile and cross-fertile with corn. It provides another novel genetic bridge for moving genes from a different Tripsacum into corn, thereby establishing a link between these wild grasses and modern corn that may be beneficial in corn improvement breeding programs.

Sun Star is distinctly different from Sun Dance and Tripsacorn in that its Tripsacum parent is a diploid rather than a tetraploid and comes from a different geographical area than the tetraploid Tripsacum plants. Therefore, previously patented plants are not intimately related to the invention of this material which used a parent plant with different qualifications. Unique propagation of Sun Star through successive generations by means of cuttings has demonstrated that the new plant has not only retained the continuous and abundant production capability, but also that its distinguishing characteristics hold true from generation to generation and appear to be firmly fixed. Propagation has taken place in Durham, N.C.

In bioassays, Sun Star shows distinct resistance to the larvae of Western corn rootworm, *Diabrotica virgifera*, as indicated by no root feeding damage and no larvae retrieved. In a field test during August, 1995, after the plant went without water for a week with temperatures exceeding 90° F. during the day, Sun Star was still green and appeared as though it had been watered; whereas, under the same conditions, Tripsacorn, Sun Dance and diploperennis suffered severe wilting and most of the vegetative growth turned brown and died. In addition to corn improvement, other obvious utility for Sun Star includes potential as a perennial forage crop on marginal land, use as a ground cover, and prolific production of novel grain.

DESCRIPTION OF ILLUSTRATIONS

This new plant is illustrated by the accompanying full color photographs which show (1) a fully grown plant showing the characteristic habit of many culms growing from the base, (2) a closeup of the culm showing red speckles, a characteristic that resembles the purple blotched effect of the $pl_1$ gene in corn, and the open sheath that does not completely enwrap the culm, a characteristic unique to Sun Star, (3) a close-up of aerial roots at a node along the culm, (4) a close-up of a leaf showing the white midrib and parallel veins, (5) a close-up of two pistillate spikes with long pilose styles showing the distichous arrangement of developing caryopses, and (6) a close-up shoeing multiple pistillate spikes borne at a single node, several are pedicellate and one is sessile.

THE PLANT

Origin: Seedling.

Parentage:

*Seed parent.—Zea diploperennis* (2n=20). Source: Jalisco, Mexico, R. Guzman M. Acc. #777.

*Pollen parent.—Tripsacum dactyloides* (2n=36). Source: K. Anderson, Manhattan, Kans.

Classification:

*Botanic.—Zea indiana* (proposed).

Chromosome number: 2n=20

Habit: Essentially erect; as many as 25 primary culms, usual number about 10.

Duration:

*Perennial.*—Sends out shoots from rhizomes. Plants will freeze at winter temperatures below 28° F., but new growth is produced in spring after winter temperatures of 0° F.

Culm:

*Height.*—Up to 1.7 meters: slender, simple with occasional branching from the nodes of the culm; glabrous; oval in cross section; diameter 1.5 cm.

*Nodes.*—Glabrous; around 12 per culm; length between nodes 10.0 cm; aerial roots develop at nodes along culm.

*Sheath.*—Not tightly closed enwrapping the culm as is typical of most Zea species, margins not united; glabrous; red speckles (Pantone #18-1860), otherwise green.

*Ligule.*—Present on adaxial side of leaf at junction of blade and sheath; length: 3.8 mm; membranaceous, irregular edge.

Leaf blade: Alternate; distichous; sheathing base; parallel veined; narrowly linear, flat, thin.

*Length.*—60 cm.

*Width.*—3.1 cm.

*Entire margin.*—Serrulate, white (Pantone #12-5202).

*Midrib.*—White (Pantone #12-5202).

*Adaxial surface.*—Hispid.

*Abaxial surface.*—Hispidulous.

*Prominent parallel veins.*—5 per 1 cm width.

INFLORESCENCE

Blooming period: Twice annually for approximately 6 weeks beginning in late September and April in North Carolina.

Monoecious: Separate male and female flowers on same plant.

Staminate flowers: May be of two types: one inflorescence type borne as paired spikelets on a slender rachis forming 7 to 37 racemes arranged in a panicle, the "tassel", at the summit of the culm. The anthers emerge and shed pollen before the styles of the pistillate spikes appear. Alternatively, staminate spikelets may be borne on a single spike above the pistillate flowers, in which case pollen shed coincides with appearance of pistillate styles on the same spike.

*Length.*—19 cm.

*Axis.*—Stiff, continuous, ascending.

Spikelet: Two-flowered, one sessile, one pedicellate; laterally compressed awnless.

*Length.*—9.5 mm.

*Width.*—2.6 mm. In pairs on one side of a persistent central hirsute axis.

*Pedicel length.*—4.5 mm.

*Glumes.*—Outer glume: cartilaginous, tapering to an acute tip, ciliate, flat, several nerved, margins scabrous. Inner glume: chartaceous.

*Anther.*—Length: 4 mm, Width: 1 mm. Color at maturity caramel (Pantone #16-1439).

Pollen viability: 98%.

Pistillate flowers: Borne in leaf axils; three or more pistillate spikelets per node, one sessile and others pedicellate; pedicel length: 1–2 cm; spikelets distichously arranged; pistillate flower consists of a single rowed spike of 6 to 10 trapezoidal caryopses in hard, shell-like fruitcases; most enclosed in a single leaf sheath, but some not enclosed; caryopses disarticulate upon maturity. Production of pistillate flowers follows anthesis of staminate flowers.

*Styles.*—Pilose.

*Color.*—Ranges from pastel parchment (Pantone #11-0603) to light lilac (Pantone #12-2903) to rose red (Pantone #18-1852) to burgundy (Pantone #19-1617).

*Length.*—80 mm.

Fruit: As many as 40 ears per culm per blooming period; flowers produced twice a year; under ideal conditions, some plants may produce over 800 ears twice annually.

Maturity: 45 days following fertilization.

Color: Most kernels are dark earth (Pantone #19-1020) with shadings of tobacco brown (Pantone #17-1327) and cashew (Pantone #17-1137). Others are sheepskin (Pantone #14-1122) to gray sand (Pantone #13-1010) with dark speckles (Pantone #19-1020 or Pantone #17-1137) and others are two-toned with a pale hardened outer glume (Pantone #14-1122) and a dark hardened inner glume (Pantone #19-1020).

Kernel (dried): Angular caryopses in hard, shell-like fruitcases, disarticulate upon maturity:

Size: Length about 6.5 mm, Width about 4.0 mm, Thickness about 3.3 mm.

Shape: Trapezoidal.

Weight: 20 seed (unsized samples): 1.2 g.

COMPARATIVE PARENTAL CHARACTERISTICS

Selected phenotypic traits of both parental species are described below, and compared to Sun Star in Table 1.

Culm: *Zea diploperennis* round in cross section; diam. 1 cm; sheath tightly closed completely enwrapping the culm; *Tripsacum dactyloides* oval in cross section; diam. 1.3 cm; sheath splits apart and does not enwrap the culm.

Leaf blade:

*Z. diploperennis.*—Length: 77.5 cm. Width: 5.0 cm; margins pink serrulate from midsection of blade to tip; adaxial surface: hirsutullous; prominent veins: 6 per 1 cm width.

*T. dactyloides.*—Length: 105 cm. Width: 2 cm; margins white serrulate along entire blade; Adaxial surface: hirsutullous; prominent veins: 8 per 1 cm width.

Blooming period: *Z. diploperinis* twice a year, end of March and end of September for about a month. *T. dactyloides* continuously from May to October.

Staminate flowers: *Z. diploperennis* borne in tassel at summit of culm. *T. dactyloides* staminate flowers borne above pistillate flowers on single spike.

Pistillate flowers: *Z. diploperennis* caryopsis triangular in hard bony fruitcases; Length: 8 mm; Width: 4.5 mm; Color: black (Pantone #10-0303), dark brown (Pantone #10-1020) or brown speckled. *T. dactyloides* caryopsis trapezoidal in hard, bony fruitcase; Length: 8.5 mm; Width: 6.5 mm. Color: pale brown (Pantone #17-1137) or buff (Pantone #13-1024).

Color reference: Leatrice Eiseman and Lawrence Herbert, *The Pantone Book of Color*. Harry N. Abrams, Publishers, New York, 1990.

TABLE 1

Comparison of Sun Star Traits with Parental Species

| | Sun Star | Diploperennis | Tripsacum |
|---|---|---|---|
| Culm | | | |
| Cross section | Round | Round | Oval |
| Diameter | 1.5 cm | 1.8 cm | 1.3 cm |
| Sheath | split | overlapping | split |
| Leaf blade | | | |
| Length | 60.0 cm | 77.5 cm | 105.0 cm |
| Width | 3.1 cm | 5.0 cm | 2.0 cm |
| Margins | white serrulate | pink serrulate | white serrulate |
| Adaxial surface | hispid | sparsely hirsute | scabrous |
| Veins | 5/cm | 6/cm | 8/cm |
| Blooming period | twice annually 6 wks. late Sept., Apr. | twice annually 4 wks. late March, late Sept. | May–Oct. |
| Staminate flowers | in tassel or borne above pistillate flowers on same spike | in tassel | above pistillate flowers on same spike |
| Pistillate flowers | | | |
| Caryopsis shape | trapezoidal | triangular-trapezoidal | trapezoidal |
| Fruitcase length | 7 mm | 8 mm | 6–10 mm |
| Fruitcase width | 5 mm | 4–5 mm | 6 mm |
| Color | dark brown to beige; speckled to two-tone | black, dark brown | beige |

COMPARISON TO SUN DANCE AND TRIPSACORN

Although Sun Star is similar to Sun Dance and Tripsacorn, it is distinctive from these plants because it was derived from pollinating a *Z. diploperennis* seed parent with a diploid *T. dactyloides* (2n=36); whereas the other two crosses used a tetraploid *T. dactyloides* (2n=72). It is distinguished from Sun Dance by its strong resistance to corn rootworm. It is different from both plants in that it produces only one type of pistillate inflorescence on a single spike, greater numbers of ears at each node, is much more prolific in seed production than Sun Dance or Tripsacorn, and has much greater tolerance to drought and heat than Sun Dance and Tripsacorn. Another characteristic difference from the other two hybrids is that the sheath is split as in its Tripsacum parent, rather than tightly enclosed around the culm. Also, Sun Star has greater fertility than the other two hybrids, as indicated by its 98% pollen viability compared to Sun Dance and Tripsacorn which are 92% and 94%, respectively. Certain Sun Star traits summarized comparatively with Sun Dance and Tripsacorn in Table 2.

TABLE 2

Comparison of Sun Star with Sun Dance and Tripsacorn.

| | Sun Star | Sun Dance | Tripsacorn |
|---|---|---|---|
| Parentage | | | |
| Seed parent | *Z. diploperennis* | *Z. diploperennis* | *T. dactyloides* |
| Chromosome no. | 2n = 20 | 2n = 20 | 2n = 72 |
| Origin | Jalisco, Acc. #777 | Jalisco, Acc. #777 | Santa Claus, IN |
| Pollen parent | *T. dactyloides* | *T. dactyloides* | *Z. diploperennis* |
| Chromosome no. | 2n = 36 | 2n = 72 | 2n = 20 |
| Origin | Manhattan, KS | Santa Claus, IN | Jalisco, Acc. #1250 |
| Culm | | | |
| Height | 1.7 m | 2.0 m | 2.0 m |
| Number | up to 25 | up to 15 | up to 35 |
| Diameter | 1.6 cm | 1.5 | 1.2 |
| Ears/culm | 5–40 | 5–10 | 5–10 |
| Sheath | split | overlapping | overlapping |
| Cross section | oval | oval | oval |
| Diameter | 1.5 cm | 1.5 | 1.2 |
| Leaf Blade | | | |
| Avg width | 3.1 | 3.3 | 3.3 |
| Avg length | 60 cm | 52 cm | 52 |
| Margins | white serrulate | red serrulate | red serrulate |
| Adaxial surface | hispid | sparsely hirsute | sparsely hirsute |
| Veins | 5/cm | 4/cm | 5/cm |
| Blooming period | twice annually 6 wks late Sept., Apr. | twice annually 4 wks late Oct., late Apr. | twice annually 4 wks late Oct., late Apr. |
| Staminate flowers | in tassel or borne above pistillate flowers on same spike | in tassel or borne above pistillate flowers on same spike | in tassel or borne above pistillate flowers on same spike |
| Spikelet length | 9.5 mm | 9.0 mm | 11.0 mm |
| Spikelet width | 2.6 mm | 2.0 mm | 3.0 mm |
| Pedicel length | 4.5 mm | 5.0 mm | 3.0 mm |
| Pollen viability | 98% | 92% | 94% |
| Pistillate flowers | | | |
| Style | pink to burgundy, pilose | pink to red, pilose | pink to red, pilose |
| Style length | 80 mm | 65 mm | 100 mm |
| Caryopsis shape | trapezoidal | triangular | triangular |
| Kernels per spike | 6–10 | 4–6 | 4–6 |
| Fruitcase length | 6.5 mm | 7.0 mm | 5.0 mm |
| Fruitcase width | 4.0 mm | 5.0 mm | 5.0 mm |
| Color | dark brown to beige; solid, speckled or two-tone | pale with brown speckles | dark brown to beige; solid or speckled |

I claim:

1. A new and distinct variety of corn plant, substantially as herein shown and described characterized by its profuse production of fruit, perennial habit, resistance to corn rootworm, and strong tolerance to drought and high temperatures.

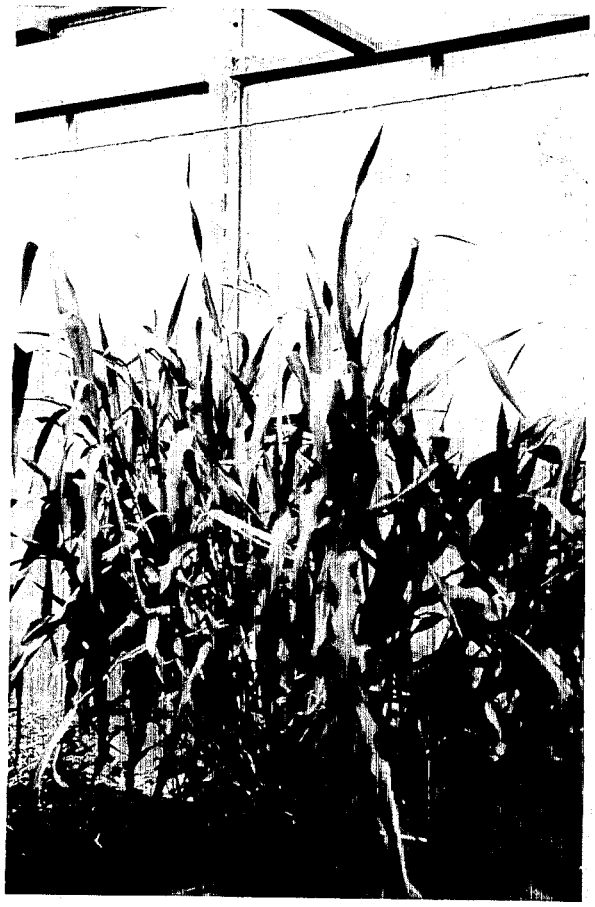

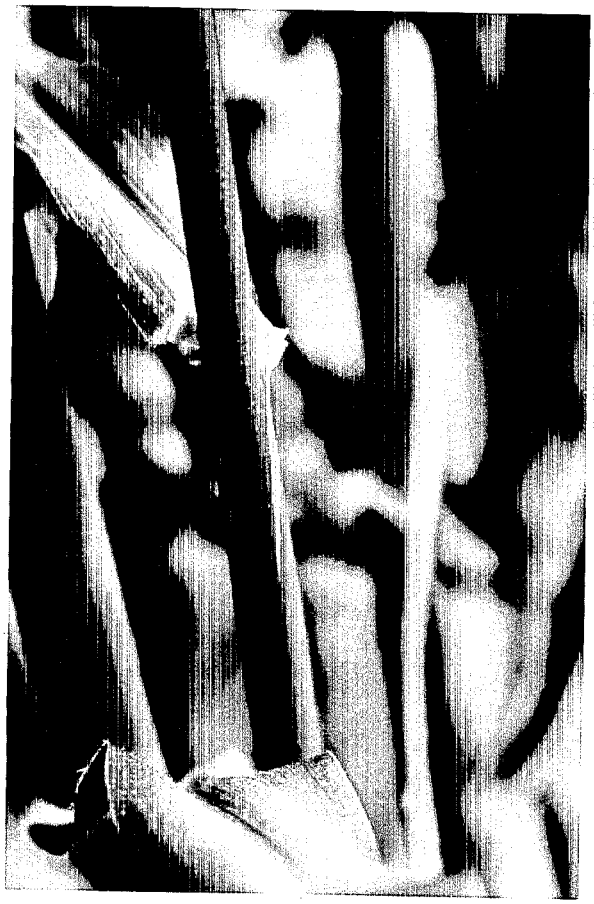

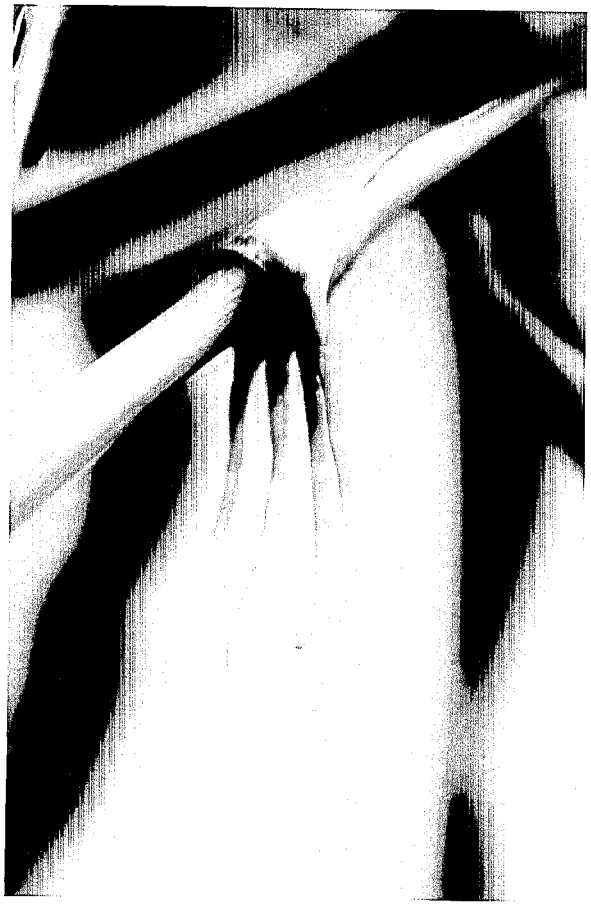

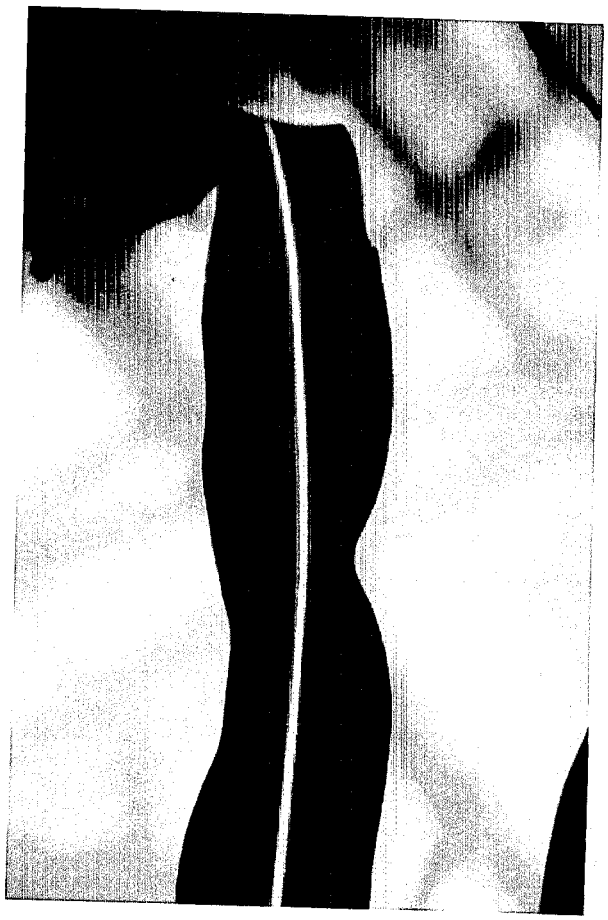

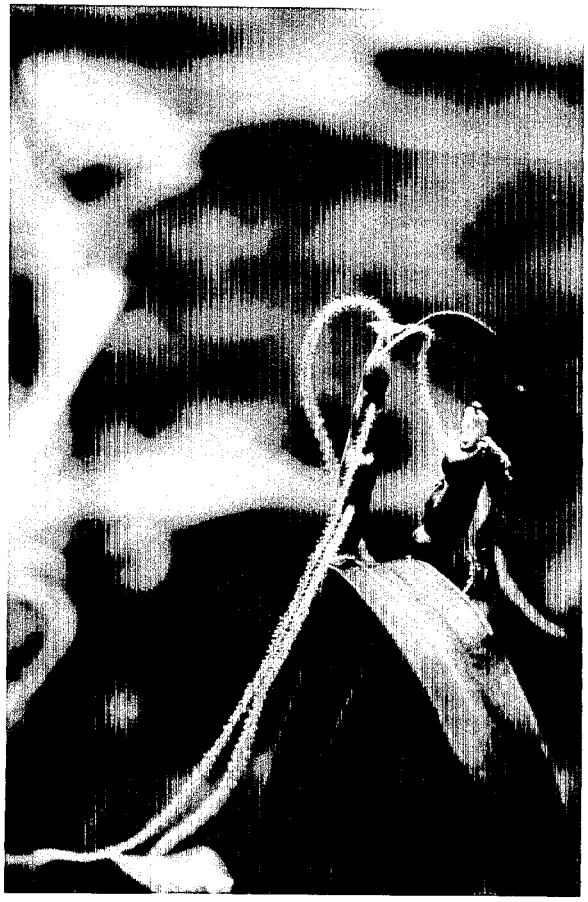

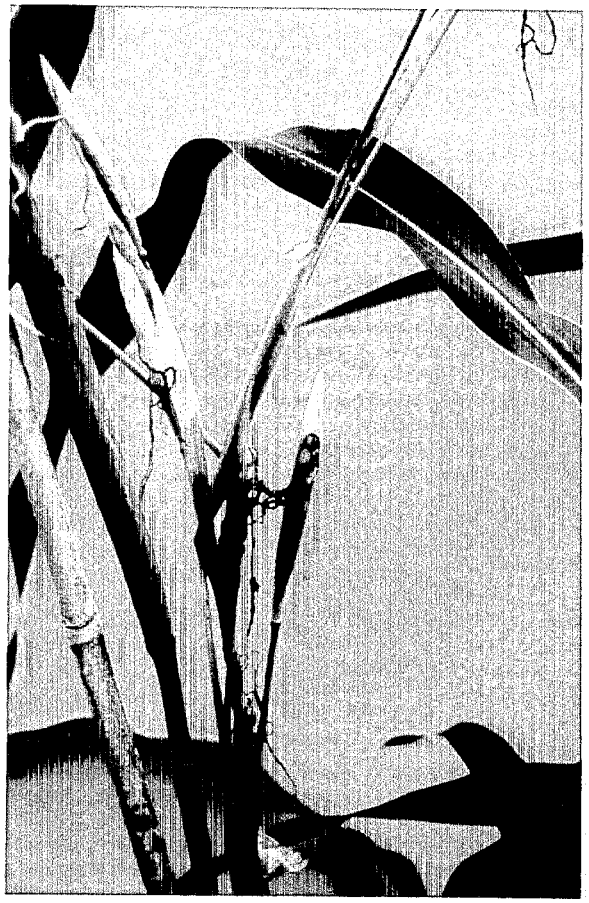

* * * * *